(12) United States Patent
Itakura et al.

(10) Patent No.: US 6,316,263 B1
(45) Date of Patent: Nov. 13, 2001

(54) METHOD FOR MEASURING ANTIOXIDANT ACTIVITIES OF SAMPLES AND METHOD FOR DIAGNOSING DIABETES OR HYPERLIPIDEMIA USING THE SAME

(75) Inventors: Hiroshige Itakura; Kazuo Kondo; Masahiro Kimura; Hiroo Yamamoto, all of Tokyo (JP)

(73) Assignee: TFB, Inc., Tokyo (JP)

( * ) Notice: Subject to any disclaimer, the term of this patent is extended or adjusted under 35 U.S.C. 154(b) by 0 days.

(21) Appl. No.: 09/318,767

(22) Filed: May 26, 1999

(30) Foreign Application Priority Data

May 26, 1998 (JP) .................................................. 10-161374

(51) Int. Cl.[7] .................................................. G01N 33/72
(52) U.S. Cl. .............................. 436/66; 436/164; 422/55
(58) Field of Search ............................ 436/66, 60, 129, 436/811, 164

(56) References Cited

U.S. PATENT DOCUMENTS

| | | | |
|---|---|---|---|
| 4,278,439 | * 7/1981 | White | 436/66 X |
| 5,620,863 | * 4/1997 | Tomasco et al. | 435/14 |
| 5,753,452 | * 5/1998 | Smith | 435/14 |
| 5,773,301 | * 6/1998 | Ziegler | 436/66 |
| 5,843,691 | * 12/1998 | Douglas et al. | 435/14 |
| 5,858,794 | * 1/1999 | Malin | 436/66 |
| 5,885,789 | * 3/1999 | Kardos et al. | 435/28 |

FOREIGN PATENT DOCUMENTS

WO 9119979   12/1991  (WO) .
WO 9210759    6/1992  (WO) .

OTHER PUBLICATIONS

Nagase et al., Serum effects, Guanidini Compounds, 2nd, Ed., pp. 317–324, 1997.*
Lissi et al., Photochemistry and Photobiology, vol. 60, No. 5, pp 405–411, 1994.*
Nakano et al., Simple Luminescence Method, Biochem and Biophys. Res. Comm., pp 940–946, Jul. 1994.*
Murray et al., Critical Care Medicine, vol. 15, No. 8, pp 797–98, 1987.*
Journal of Environmental Science and Health, A20(1), 21–35 (1985), John Kemp et al.
Chem. abstr., vol. 123, No. 5, Jul. 31, 1995 (Columbus, OH, USA), p. 490, col. 2.
Miller, N.J. et al. "Total antioxidant activity of low density lipoproteins and the relationship with alpha–tocopherol status", FEBS Lett. 1995, 365(2,3), 164–6 (Eng).
Jaworowski, A. et al. "Calponin reduces shortening velocity in skinned taenia coli smooth muscle fibres", FEBS Lett. 1995, 365, 167–171 (Sweden).

* cited by examiner

Primary Examiner—Maureen M. Wallenhorst
(74) Attorney, Agent, or Firm—Birch, Stewart, Kolasch & Birch, LLP

(57) ABSTRACT

A method for measuring antioxidant activity of test samples, which attains higher sensitivity than the conventional methods is disclosed. In the method of this invention, methemoglobin, an oxidizing agent which oxidizes methemoglobin, a coloring agent which generates color by reaction with methemoglobin in the presence of the oxidizing agent, and a test sample whose antioxidant activity is to be measured are reacted, and the generated color is measured.

7 Claims, 4 Drawing Sheets

METHOD FOR MEASURING ANTIOXIDANT ACTIVITIES OF SAMPLES AND METHOD FOR DIAGNOSING DIABETES OR HYPERLIPIDEMIA USING THE SAME

BACKGROUND OF THE INVENTION

I. Field of the Invention

The present invention relates to a method for measuring antioxidant activities of samples and method for diagnosing diabetes or hyperlipidemia using the same.

II. Description of the Related Art

Methods for measuring antioxidant activities of samples, that is, the activities to prevent oxidation of other substances, are known. For example, WO92/10759 discloses a method for measuring antioxidant activity of blood plasma for the purpose of diagnosing myocardial infarction or for diagnosing conditions of a patient for the likelihood of onset of myocardial infarction. In this method, blood plasma which is a test sample, metmyoglobin, hydrogen peroxide, a coloring agent such as 2,2'-azinobis(3-ethylbenzthiazoline 6-sulfonate) (hereinafter referred to as "ABTS") are reacted and the absorbance after the reaction is measured. With this method, if the antioxidant activity of blood plasma is high, oxidation of metmyoglobin by hydrogen peroxide is inhibited by the blood plasma, so that coloring is inhibited. On the other hand, if the antioxidant activity of the blood plasma is low, oxidation of metmyoglobin by hydrogen peroxide is not inhibited very much, so that coloring is not inhibited very much accordingly. Therefore, by measuring the absorbance of the reaction mixture after the reaction, the antioxidant activity of the blood plasma can be measured.

Needless to say, it is advantageous to provide a method for measuring antioxidant activities of test samples, whose sensitivity is higher than that of the above-mentioned conventional method.

SUMMARY OF THE INVENTION

Accordingly, an object of the present invention is to provide a method for measuring antioxidant activities of test samples, whose sensitivity is higher than that of the conventional method.

The present inventors intensively studied to discover that by using methemoglobin in place of metmyoglobin used in the conventional method, the sensitivity of the measurement is increased by not less than three times, thereby completing the present invention.

That is, the present invention provides a method for measuring antioxidant activity of a test sample comprising the steps of reacting methemoglobin, an oxidizing agent which oxidizes methemoglobin, a coloring agent which generates color by reaction with methemoglobin in the presence of said oxidizing agent, and a test sample whose antioxidant activity is to be measured; and measuring the generated color. The present invention also provides a method for diagnosing diabetes or hyperlipidemia comprising carrying out the above-described method of the present invention using a body fluid such as blood plasma or serum as the test sample.

By the present invention, a method for measuring antioxidant activities of test samples, whose sensitivity of measuring antioxidant activities of test samples is higher than that of the conventional method, was provided. Further, by the present invention, a highly sensitive diagnostic method for diabetes or hyperlipidemia was provided.

DETAILED DESCRIPTION OF THE PREFERRED EMBODIMENTS

Figure 1:
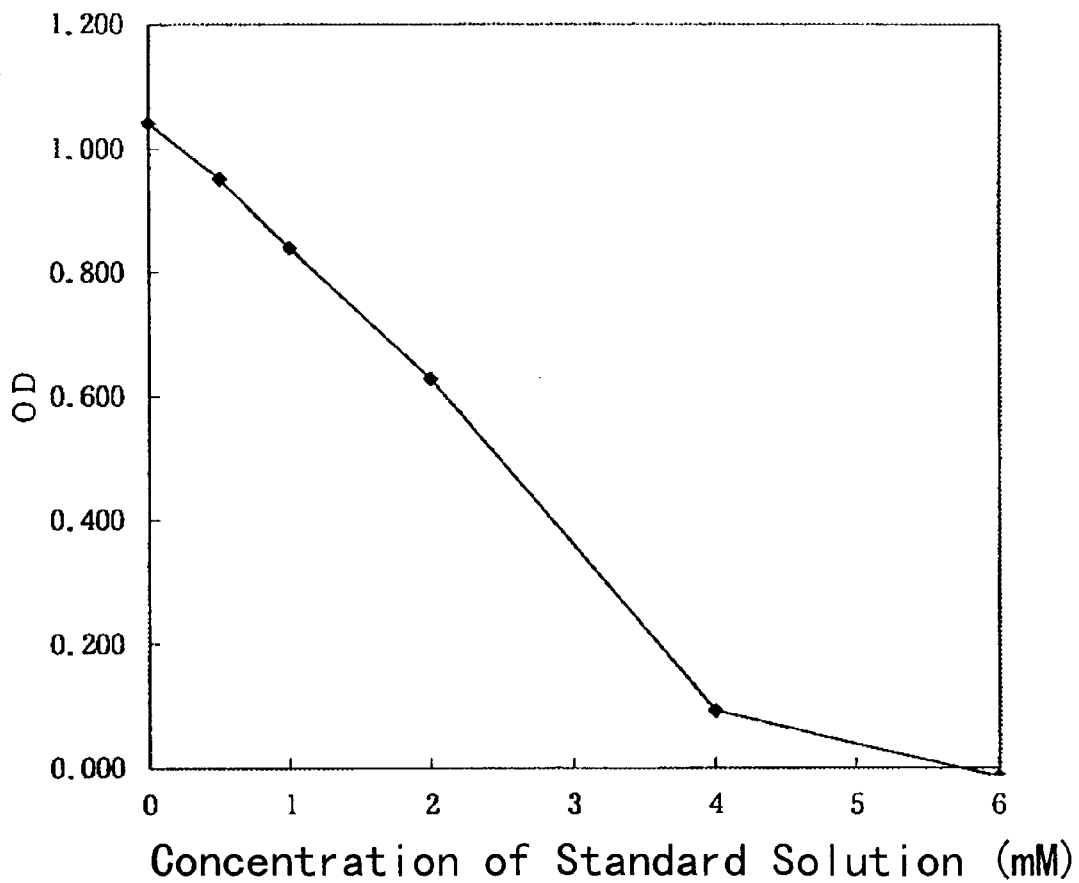
FIG. 1 shows a calibration curve prepared according to the method of the present invention using standard solutions having known concentrations.

The methemoglobin used in the present invention may be originated either from human or from an animal other than human. Methemoglobin may easily be prepared by oxidizing hemoglobin according to a conventional method. Alternatively, commercially available methemoglobin may also be employed. Further, since methemoglobin is generated by oxidation of hemoglobin, hemoglobin may be used as a starting material of the reaction in the method of the present invention, and methemoglobin generated in the reaction system by oxidation of the hemoglobin may be used as the methemoglobin in the present invention. Thus, in the reaction system comprising methemoglobin, an oxidizing agent, a coloring agent and a test sample, hemoglobin may be employed in place of methemoglobin.

Although the concentration of methemoglobin in the reaction mixture is not restricted, in view of high sensitivity, the concentration of methemoglobin may preferably be 0.2 $\mu$M to 8 $\mu$M, more preferably 0.5 $\mu$M to 1.5 $\mu$M.

As the oxidizing agent used in the method of the present invention, any oxidizing agent may be employed as long as it can oxidize methemoglobin so as to make the methemoglobin generate color by the reaction with the coloring agent hereinafter described. Preferred examples of the oxidizing agent include hydrogen peroxide, oxoacids and salts thereof, but the oxidizing agents are not restricted thereto.

The concentration of the oxidizing agent in the reaction mixture is not restricted and may appropriately be selected by a routine experiment depending on the type of the oxidizing agent used. In cases where hydrogen peroxide is used, in view of attaining high sensitivity, the concentration of hydrogen peroxide in the reaction mixture may preferably be 40 $\mu$M to 200 $\mu$M, more preferably 60 $\mu$M to 150 $\mu$M.

As the coloring agent used in the method of the present invention, any coloring agent which generates color by reaction with methemoglobin in the presence of the above-described oxidizing agent may be employed. Preferred examples of the coloring agent include ABTS and salts thereof, o-phenylenediamine (OPD), tetramethylbenzidine (TMB), diaminobenzidine (DAB), 4-chloronaphthol, 5-aminosalicylic acid, o-toluidine, o-dianisidine and the like.

The concentration of the coloring agent in the reaction mixture is not restricted and may appropriately be selected depending on the type of the coloring agent by a routine experiment. In cases where ABTS is used, in view of attaining high sensitivity, the concentration of ABTS in the reaction mixture may preferably be not less than 50 $\mu$M, more preferably not less than 80 $\mu$M. Even if ABTS is added to a concentration of not less than 300 $\mu$M, the sensitivity is no longer increased and addition of ABTS to a concentration of not less than 300 $\mu$M is wasteful. Thus, the concentration of ABTS is preferably not more than 300 μM. However, since the reaction is not adversely affected by high concentration of ABTS, the concentration of ABTS may be as high as, for example, about 1 mM.

The test sample employed in the method of the present invention may be any sample whose antioxidant activity is to be measured. Examples of the test sample include body fluids such as blood plasma and serum, various foods, beverages and chemical substances. The test sample may be mixed with other reagents after being diluted appropriately as required.

In carrying out the reaction, the above-described three reagents and the test sample are mixed. Each of the three reagents may preferably be in the form of a solution in buffer or water. Although the order of mixing the reagents and the test sample is not restricted, in order to assure that the test sample exists in the place of reaction between the oxidizing agent and methemoglobin, it is preferred to firstly mix methemoglobin, the coloring agent and the test sample, and to finally add the oxidizing agent.

The reaction temperature is not restricted and may preferably be from room temperature to about 40° C., more preferably 25° C. to 35° C. The reaction time varies depending on the reaction temperature and the preferred reaction time may appropriately be selected by a routine experiment. Usually, the reaction time may preferably be about 2 to 20 minutes, more preferably about 5 to 15 minutes. Even if the reaction time is longer than 20 minutes, the reaction is not adversely affected.

After the reaction, the generated color is measured. This may be carried out easily by, for example, measuring absorbance of the reaction mixture. In this case, the wavelength of the light used for measuring the absorbance is appropriately selected depending on the coloring agent used. In cases where ABTS is used as the coloring agent, the wavelength may preferably be about 550 nm to 870 nm, more preferably about 734 nm. Alternatively, a wavelength from 390 nm to 420 nm may also be employed.

According to the method of the present invention, if the antioxidant activity of the test sample is high, oxidation of methemoglobin by the oxidizing agent is well inhibited by the test sample, so that coloring is inhibited. On the other hand, if the antioxidant activity of the test sample is low, oxidation of methemoglobin by the oxidizing agent is not inhibited very much, so that coloring is not inhibited very much accordingly. Therefore, by measuring the absorbance of the reaction mixture after the reaction, the antioxidant activity of the test sample can be measured.

The antioxidant activity of an unknown test sample in terms of the amount of a particular standard substance may be measured by preliminarily preparing a calibration curve (concentration of standard sample is taken along the abscissa and the absorbance of the test sample is taken along the ordinate), measuring the absorbance using the unknown test sample, and comparing the measured absorbance with the calibration curve.

The method of the present invention may be used for various purposes. For example, by employing a body fluid such as blood plasma or serum as the test sample, diagnosis of diabetes or hyperlipidemia may be carried out. That is, as concretely described in the Examples below, since the antioxidant activities of the body fluids of patients suffering from diabetes are lower than those of normal individuals, diagnosis of diabetes and hyperlipidemia can be attained by measuring the antioxidant activity of a body fluid such as blood plasma or serum by the method of the present invention. Further, relationships between oxidative properties of foods or beverages and carcinogenecities thereof are now suspected. By measuring the antioxidant activities of various foods and beverages by the method according to the present invention, the antioxidative performance of a food or beverage for decreasing the oxidative property of other foods and beverages can be known. Therefore, the present invention is helpful for screening foods and beverages which may be helpful for prevention of cancers.

The present invention will now be described by way of Examples thereof. It should be noted, however, the Examples are presented for the illustration purpose only and should not be interpreted in any restrictive way.

EXAMPLE 1

Preparation of Calibration Curve

Solutions in phosphate buffer of methemoglobin (purchased from Sigma), ABTS diammonium salt (purchased from Aldrich) and hydrogen peroxide were prepared. As standard solutions, 6-hydroxy-2,5,7,8-tetramethylchroman-2carboxylic acid (trademark Trolox, purchased from Tokyo Kasei), which is an α-tocopherol derivative, in phosphate buffer, with varying concentrations of 0, 0.5, 1.0, 2.0, 4.0 and 6.0 mM, respectively, were prepared.

Two hundred and fifty microliters of ABTS solution and 250 μl of methemoglobin solution were mixed and 60 μl of a standard solution was added to the mixture. Hydrogen peroxide solution was then added to the mixture to start oxidation reaction. The concentrations of methemoglobin, ABTS and hydrogen peroxide in the reaction mixture were 2 μM, 400 μM and 130 μM, respectively. The reaction was carried out at 30° C. Ten minutes later, the absorbance at 734 nm was measured. The results are shown in FIG. 1.

As shown in FIG. 1, the higher the concentration of the standard solution, the smaller the absorbance. Thus, it can be seen that oxidation of methemoglobin is inhibited by the antioxidative action of Trolox (trademark) so that the degree of coloring is made small accordingly. Since the absorbance is continuously decreased with the increase of the concentration of the standard solution, it can be seen that the antioxidant activity of a test sample can be measured by the method of the present invention.

EXAMPLE 2

Detection Limit in Low Concentration Region

The same procedure as in Example 1 was repeated except that the concentrations of the Trolox (trademark) solutions were 0, 0.04, 0.08, 0.12 and 0. 16 mM, respectively, and the reaction time was 3 minutes. The experiments were repeated five times for each concentration. The results are shown in FIG. 2.

Figure 2:
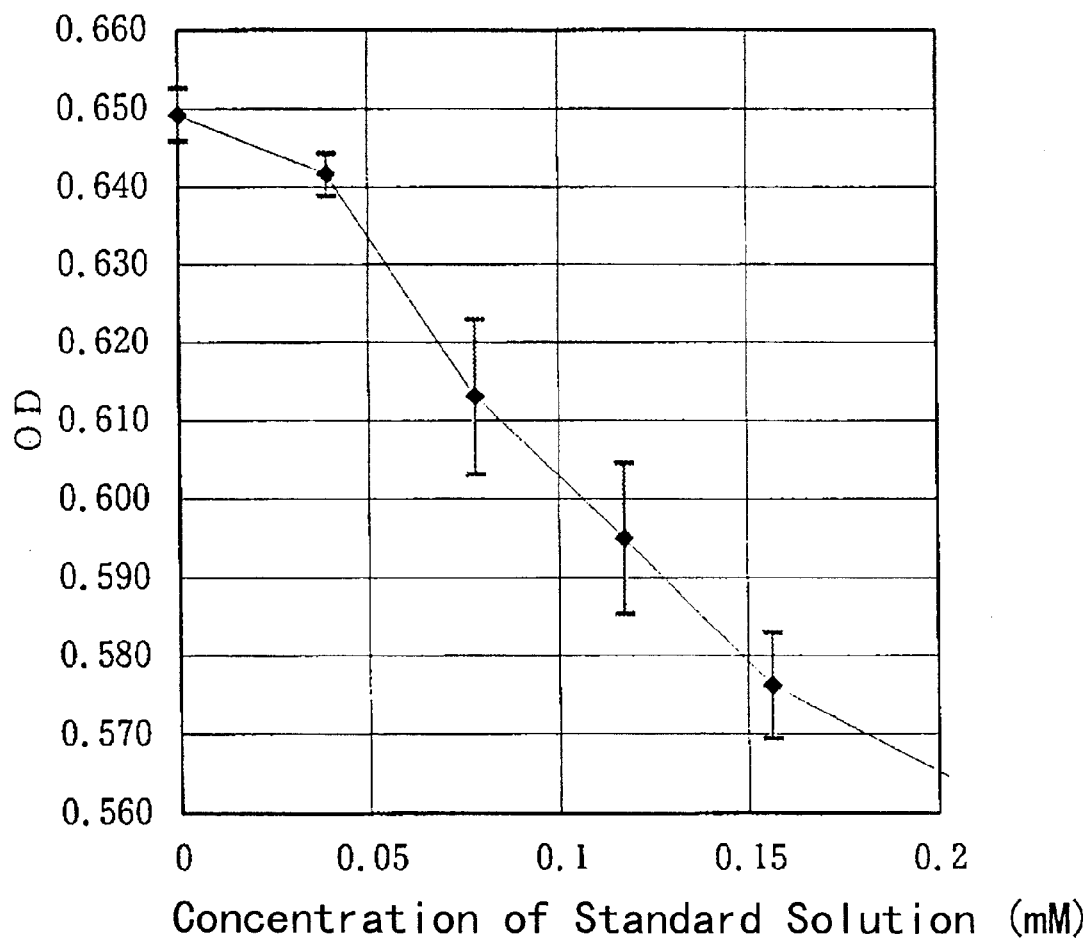
FIG. 2 shows the average values and ranges of ±2SD of the values measured by the method according to the present invention using standard solutions having low concentrations.

FIG. 2, each average of the values measured by the 5 runs is indicated by solid square, and the range of ±twice of standard deviation (±2SD) is indicated by a vertical bar. According to the ±2SD method which is a common method for determining the detection limit, the minimum concentration of the standard solution at which the ±2SD range of the measured value does not overlap with the ±2SD range of the measured value when the concentration of the standard solution is zero is defined as the detection limit. From FIG. 2, it can be seen that the detection limit of this method is about 0.04 mM of Trolox (trademark).

Comparative Example 1

Detection Limit (1) of Conventional Method Using Metmyoglobin

The same procedure as in Example 2 was repeated except that metmyoglobin was used in place of methemoglobin. The results are shown in FIG. 3.

Figure 3:
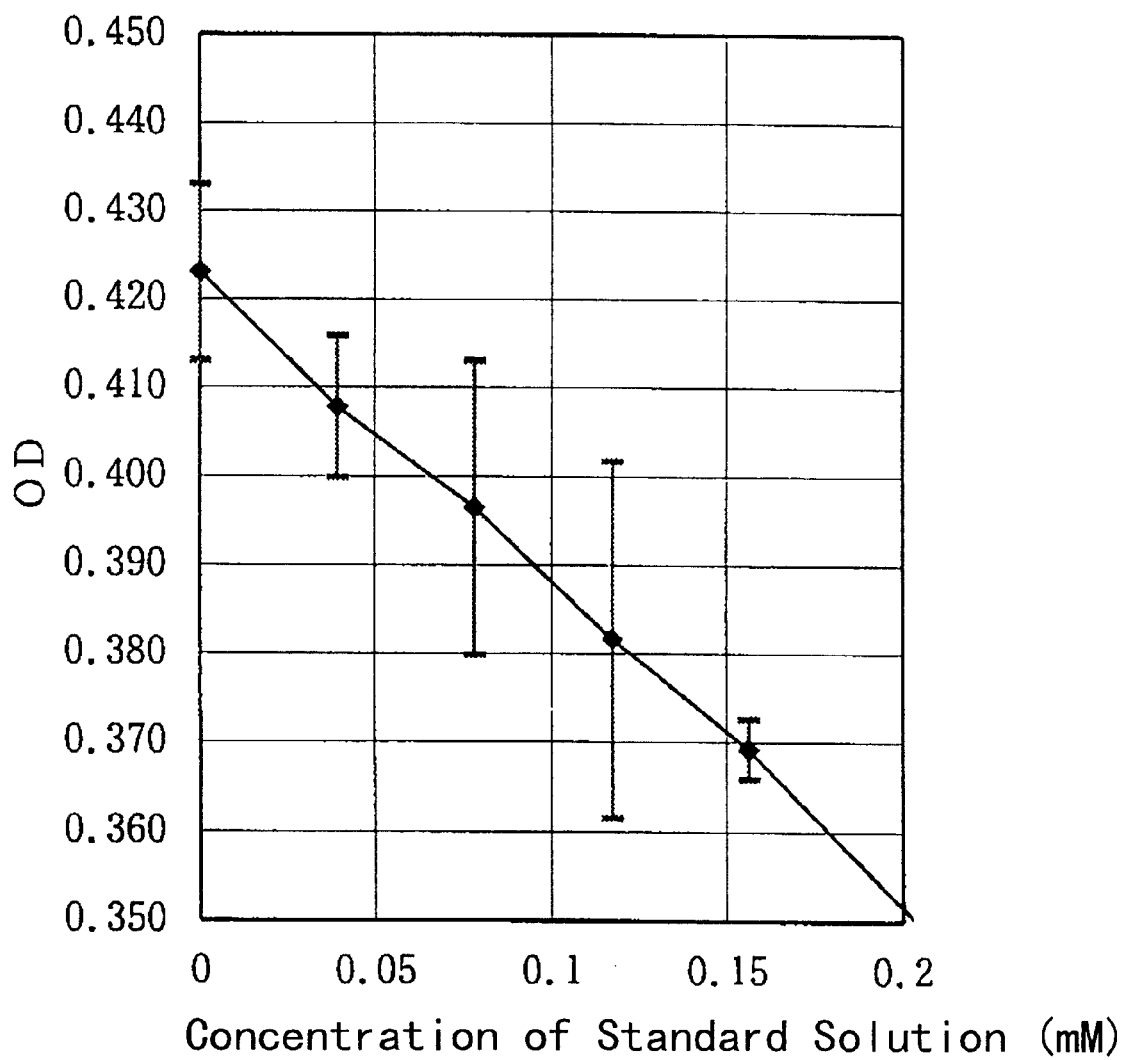
FIG. 3 shows the average values and ranges of ±2SD of the values measured by the conventional method employing metmyoglobin in place of methemoglobin, using standard solutions having low concentrations.

From FIG. 3, it can be seen that the detection limit determined by the ±2SD method was about 0.12 mM of Trolox (trademark). This detection limit was three times of the detection limit of the method according to the present invention described in Example 2.

Comparative Example 2

Detection Limit (2) of Conventional Method Using Metmyoglobin

The same procedure as in Comparative Example 1 was repeated except that the concentrations of metmyoglobin, ABTS and hydrogen peroxide in the reaction mixture were 5 μM, 500 μM and 250 μM, respectively. The results are shown in FIG. 4.

Figure 4:
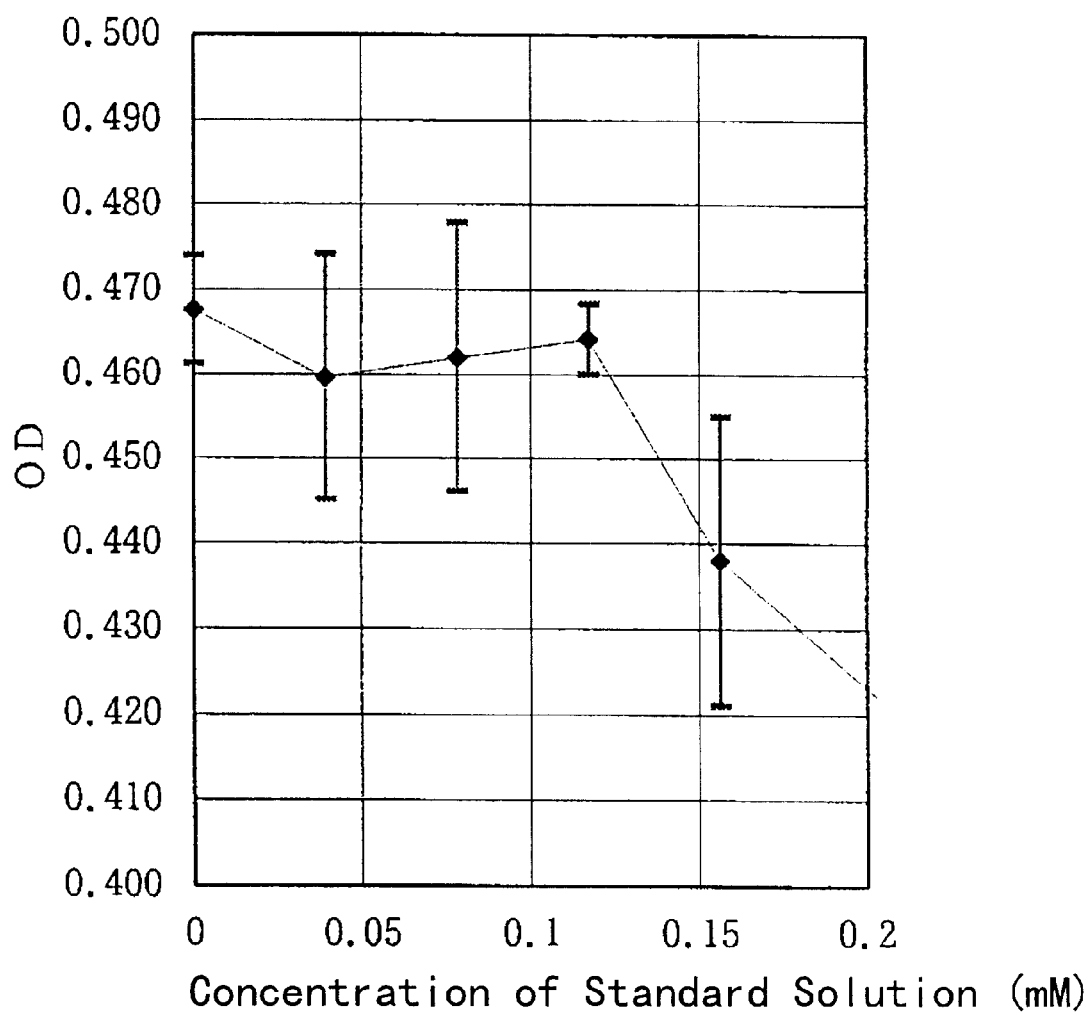
FIG. 4 shows the average values and ranges of ±2SD of the values measured by the conventional method employing metmyoglobin in place of methemoglobin, using standard solutions having low concentrations.

It can be seen from FIG. 4 that the detection limit determined by the ±2SD method was about 0.16 mM of Trolox (trademark). This detection limit is four times that of the method of the present invention described in Example 2.

EXAMPLE 3

Measurement of Antioxidant Activity of Human Blood Plasma

The same procedure as in Example 1 was repeated except that blood plasmas of normal individuals, patients suffering from diabetes and patients suffering from hyperlipidemia were used as the test samples. By comparing the measured values with the calibration curve prepared in Example 1, the antioxidant activity of each test sample in terms of the concentration of Trolox (trademark) was determined. The results are shown in Table 1 below.

TABLE 1

| Test Sample | Concentration in terms of Trolox (trademark) (mM) |
| --- | --- |
| Hyperlipidemia (1) | 5.14 |
| Hyperlipidemia (2) | 5.27 |
| Hyperlipidemia (3) | 5.10 |
| Hyperlipidemia (4) | 5.27 |
| Diabetes (1) | 5.33 |
| Diabetes (2) | 5.47 |
| Normal Individual (Male) | 5.62 |
| Normal Individual (Female) | 5.52 |

As can be seen from Table 1, the antioxidant activities of the blood plasmas of the patients suffering from hyperlipidemia or diabetes were lower than those of the normal individuals. Thus, it can be seen that hyperlipidemia and diabetes may be diagnosed by applying the method of the present invention.

EXAMPLE 4

Measurement of Antioxidant Activities of Beverages

Antioxidant activities of Japanese tea, black tea, coffee, red wine and white wine were measured. The test sample of Japanese tea or black tea was prepared by adding 100 ml of boiled water at 100° C. to 6 g of tea leaf, leaving the resultant to stand for 1 minute, recovering the supernatant and diluting the supernatant (64-fold for Japanese tea and 32-fold for black tea). The test sample of coffee was prepared by adding 60 ml of boiled water at 100° C. to 6 g of ground coffee beans, leaving the resultant to stand for 1 minute, recovering the supernatant and 32-fold diluting the supernatant. The test samples of red wine and white wines were prepared by 16-fold diluting the wine.

The same procedure as in Example 1 was repeated except that each of the above-described samples was used in place of the standard solution. The antioxidant activity of each of the non-diluted samples in terms of the concentration of Trolox (trademark) was determined by comparing the measured value with the calibration curve prepared in Example 1 and compensation for the dilution. The results are shown in Table 2 below.

TABLE 2

| Beverage | Concentration in terms of Trolox (trademark) (mM) |
| --- | --- |
| Japanese tea | 66.56 |
| Black tea | 36.16 |
| Coffee | 25.56 |
| Red Wine | 23.68 |
| White Wine | 1.44 |

We claim:
1. A method for determining antioxidant activity of a test sample comprising the steps of reacting methemoglobin, an oxidizing agent which oxidizes methemoglobin, a coloring agent which generates color by reaction with methemoglobin in the presence of said oxidizing agent, and a test sample whose antioxidant activity is to be measured; measuring any generated color and determining the antioxidant activity of the test sample based upon the amount of color measured, wherein the more color that is measured, the lower the antioxidant activity of the test sample and vice-versa.

2. The method according to claim 1, wherein said oxidizing agent is hydrogen peroxide.

3. The method according to claim 1, wherein said coloring agent is 2,2'-azinobis(3-ethylbenzthiazoline 6-sulfonate).

4. A method for diagnosing diabetes comprising carrying out the method according to claim 1 wherein said test sample is a body fluid, and diabetes is diagnosed in a test individual when the antioxidant activity of a body fluid from the test individual is lower than the antioxidant activity of a body fluid from a normal individual.

5. The method according to claim 4 wherein said body fluid is blood plasma or serum.

6. A method for diagnosing hyperlipidemia comprising carrying out the method according to claim 1 wherein said test sample is a body fluid, and hyperlipidemia is diagnosed in a test individual when the antioxidant activity of a body fluid from the test individual is lower than the antioxidant activity of a body fluid from a normal individual.

7. The method according to claim 6 wherein said body fluid is blood plasma or serum.

* * * * *